(12) United States Patent
Weidmann

(10) Patent No.: US 7,468,441 B2
(45) Date of Patent: Dec. 23, 2008

(54) 1-IMIDAZOLYMETHYL-SUBSTITUTED-2-NAPHTOLS AND THEIR USE AS ACCELERATORS FOR LOW-TEMPERATURE CURING

(75) Inventor: Ulrich Weidmann, Basel (CH)

(73) Assignee: Hunstman Advanced Materials Americas Inc., The Woodlands, TX (US)

( * ) Notice: Subject to any disclaimer, the term of this patent is extended or adjusted under 35 U.S.C. 154(b) by 211 days.

(21) Appl. No.: 10/552,902

(22) PCT Filed: Apr. 13, 2004

(86) PCT No.: PCT/EP2004/050501

§ 371 (c)(1),
(2), (4) Date: Oct. 13, 2005

(87) PCT Pub. No.: WO2004/092141

PCT Pub. Date: Oct. 28, 2004

(65) Prior Publication Data

US 2006/0211845 A1 Sep. 21, 2006

(30) Foreign Application Priority Data

Apr. 16, 2003 (CH) .................................. 0696/03

(51) Int. Cl.
*C07D 233/00* (2006.01)
*C08G 59/68* (2006.01)
(52) U.S. Cl. ...................... 548/335.1; 548/100; 528/408
(58) Field of Classification Search ................ 548/100, 548/335.1, 339.5, 340.1; 528/408
See application file for complete search history.

(56) References Cited

U.S. PATENT DOCUMENTS

| | | | |
|---|---|---|---|
| 3,356,645 A | | 12/1967 | Warren |
| 3,914,236 A | * | 10/1975 | Lerch et al. .................. 546/143 |
| 4,101,514 A | | 7/1978 | Thom |
| 4,463,011 A | * | 7/1984 | Ogata et al. .................. 514/397 |
| 4,487,914 A | | 12/1984 | Barton |

(Continued)

FOREIGN PATENT DOCUMENTS

| | | |
|---|---|---|
| CH | 648844 A5 * | 4/1985 |
| EP | 0761709 | 3/1997 |

\* cited by examiner

*Primary Examiner*—Mark Eashoo
*Assistant Examiner*—Megan McCulley

(57) ABSTRACT

Compounds of the general formulae (I) and (II): where $R_1$, $R_2$ and $R_3$ each independently of one another are H; $C_{1-17}$alkyl; $C_{3-12}$cycloalkyl, optionally substituted by $C_{1-4}$alkyl groups; $C_{4-20}$cycloalkyl-alkyl, optionally substituted by $C_{1-4}$alkyl groups; $C_{6-10}$, aryl, optionally substituted by 1-3 $C_{1-4}$alkyl groups, —CN, Hal, OH, or $C_{1-10}$alkoxy; $C_{7-15}$phenylalkyl, optionally substituted by 1-3 $C_{1-4}$alkyl groups; $C_{3-12}$alkenyl; $C_{3-12}$alkynyl; or aromatic or aliphatic $C_{3-12}$acyl; $R_4$, $R_5$, $R_6$, $R_7$, $R_8$, and $R_9$ each independently of one another are H; $C_{1-17}$alkyl, $C_{3-12}$cycloalkyl, optionally substituted by $C_{1-4}$alkyl groups; $C_{4-20}$cycloalkyl-alkyl, optionally substituted by $C_{1-4}$alkyl groups; $C_{6-10}$aryl, optionally substituted by 1-3 $C_{1-4}$alkyl groups; $C_{7-15}$phenylalkyl, optionally substituted by 1-3 $C_{1-4}$alkyl groups; $C_{3-17}$alkenyl; $C_{3-12}$alkynyl; $C_{1-12}$alkoxy; or OH; for formula (1) R is $C_{1-12}$alkyl; $C_{3-12}$cycloalkyl, optionally substituted by $C_{1-4}$alkyl groups; $C_{4-20}$cycloalkyl-alkyl; optionally substituted by $C_{1-4}$alkyl groups; $C_{6-10}$aryl, optionally substituted by 1-3 $C_{1-4}$alkyl groups; $C_{7-15}$phenylalkyl, optionally substituted by 1-3 $C_{1-4}$alkyl groups; $C_{3-12}$alkenyl; or $C_{3-12}$alkynyl; and for formula (II) n=2-12; as accelerators in curable epoxy resin compositions which are used as a compression moulding compound, sinter powder, encapsulating system, or casting resin, or for producing prepregs and laminates having very good interlaminar shear strength values using the resin infusion method, wet layup method and injection methods, for producing components, especially components of large surface area.

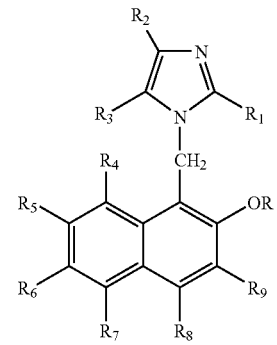

(I)

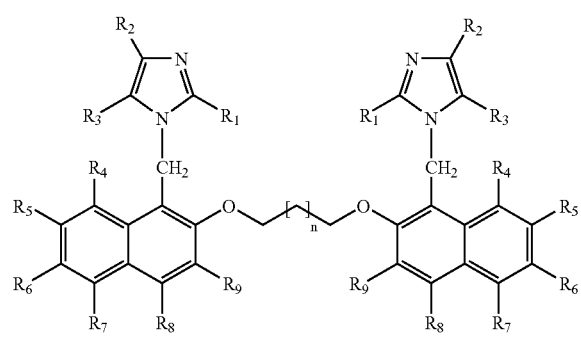

(II)

13 Claims, No Drawings

U.S. PATENT DOCUMENTS

| | | |
|---|---|---|
| 4,549,008 A | 10/1985 | Renner |
| 4,602,022 A * | 7/1986 | Cozzi et al. ................. 514/337 |
| 4,649,181 A | 3/1987 | Darms |
| 4,666,954 A * | 5/1987 | Forgo et al. ................... 522/83 |
| 4,677,170 A | 6/1987 | Monnier |
| 5,001,212 A | 3/1991 | Hammer |
| 5,134,111 A * | 7/1992 | Okita et al. ................. 562/466 |
| 5,298,649 A * | 3/1994 | Okita et al. ................... 560/56 |
| 5,591,811 A * | 1/1997 | Blyakhman .................. 525/504 |
| 6,245,835 B1 * | 6/2001 | Klein et al. .................. 523/402 |
| 6,555,690 B2 * | 4/2003 | Johnson et al. ............. 546/309 |
| 6,713,632 B1 * | 3/2004 | Kawakami ............... 548/335.1 |
| 7,323,485 B2 * | 1/2008 | Chow et al. ................. 514/396 |
| 2002/0111422 A1 * | 8/2002 | Back et al. .................. 524/602 |
| 2004/0009976 A1 * | 1/2004 | Takeuchi et al. ......... 514/228.2 |
| 2006/0247259 A1 * | 11/2006 | Funahashi et al. ........ 514/265.1 |

1-IMIDAZOLYMETHYL-SUBSTITUTED-2-NAPHTOLS AND THEIR USE AS ACCELERATORS FOR LOW-TEMPERATURE CURING

CROSS REFERENCE TO RELATED APPLICATIONS

This application is the National Phase of International Application PCT/EP2004/050501 filed Apr. 13, 2004 which designated the U.S. and which claims priority to Swiss Pat. App. No. 0696/03 filed Apr. 16, 2003. The noted applications are incorporated herein by reference.

The invention relates to novel Mannich bases based on 1-imidazolylmethyl-substituted 2-naphthol compounds and also to their use as accelerators for epoxy resin systems which allow high ILS values in laminates, particularly for impregnation by resin infusion methods, the wet layup method and other impregnating methods. The accelerators of the invention are additionally suitable for sinter powder, casting resin and compression moulding compound applications.

The compound 1-imidazolylmethyl-2-naphthol and other imidazole catalysts and accelerators in connection with epoxy resins are known.

The customarily used imidazoles such as imidazole, 1-methylimidazole, 2-methylimidazole, 2-ethyl-4-methylimidazole or else 2-phenylimidazoles, however, in many epoxy resin formulations produce inadequate storage stabilities of prepregs at room temperature when they are employed in prepreg formulations.

In the past attempts have been made to solve this problem by looking to reduce the reactivity of the imidazoles by formation of salts with organic or inorganic acids: see U.S. Pat. Nos. 3,356,645 and 5,001,212, for example. Although improvements in the storage stabilities of prepregs (standing times for short) were achieved in those cases, they are still not sufficient for many applications.

Another way of improving the standing times of prepregs is to form imidazole complexes by reacting imidazoles with metal salts: see U.S. Pat. Nos. 4,101,514 and 4,487,914, for example. Generally speaking, the improvement in the standing times that can be achieved in this way is obtained at the expense of an increase in the processing temperatures. Moreover, the metal complexes present in the cured epoxy resin system lead to a deterioration in the dielectric values and also to an increase in the water absorption. In many applications, however, it is required that there is no substantial change in water absorption, since otherwise the glass transition temperature may be lowered, which can lead to a considerable change in the mechanical, electrical and thermal properties of the impregnated component.

EP 0 761 709 describes 1-imidazolylmethyl-substituted 2-naphthol compounds as catalysts which make it possible substantially to avoid the disadvantages described in the above citations. The compounds in question are stable Mannich bases which in epoxy resin systems lead to a markedly improved standing time of the overall system at room temperature. A formulation comprising such a catalyst can be cured rapidly in the temperature range between 110° C. and 150° C. Materials of this kind exhibit good mechanical properties with relatively high glass transition ranges. Prepregs comprising such catalysts can be stored without problems for up to 16 days at room temperature and processed to laminates.

Established methods for producing favourably priced components of large surface area include resin infusion methods and other impregnating methods. In order to be able to be used in resin infusion methods, such as RTM, the epoxy resin formulation for use ought to have a viscosity of between 100 and 1000 mPa·s, but preferably from 100 mPa·s to 500 mPa·s, at a temperature of from 23° C. to 60° C. For reasons of cost, the aim is for temperatures below 100° C. during the impregnating operation. When, for example, the wet layup method is chosen for components of large surface area, the curing temperatures ought to remain well below 100° C., again on economic grounds. For reasons of greater ease of handling the semi-finished products manufactured in this way (prepregs) ought to have a relatively long storage stability at room temperature, which means that the prepreg must be capable of troublefree conversion to the laminate after storage for, for example, four days or more. Where laminates produced in this way are employed in energy-producing installations, the laminates being subject to rotational movements and considerable shear forces during their use, a certain minimum of adhesion is necessary between the individual layers which make up the laminate. One measure of this adhesion is that known as interlaminar shear strength, also called ILS for short, which is determined in accordance with the ASTM standard (ASTM D 2344-84). A maximum ILS value is therefore an aim for such applications.

It has now been found that 1-(imidazolyl-2-methyl)-2-naphthol does enable outstanding storage stabilities at room temperature in prepreg formulations but not very high interlaminar shear strength values. The maximum achievable value is approximately 22 MPa, irrespective of whether curing is carried out at 60° C. for four hours, at 75° C. for four hours or even eight hours or at 140° C. for 30 minutes.

It has now surprisingly been found that Mannich bases based on 1-imidazolylmethyl-substituted 2-naphthol compounds, whose free aromatic hydroxyl group is alkylated, have a profile of properties which allows their advantageous use as accelerators for epoxy resin systems particularly for the resin infusion method, the wet layup method and impregnating methods, since semi-finished articles impregnated in this way, in addition to a prepreg storage stability of 2-8 days, also give ILS values of up to 50 MPa when cured at 60° C. or 75° C. for from four to eight hours.

The present invention accordingly first provides compounds of the general formulae (I) and (II):

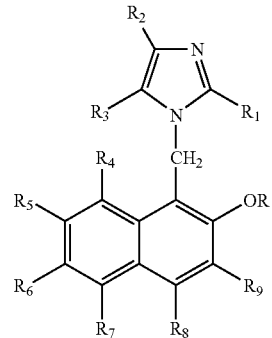

(I)

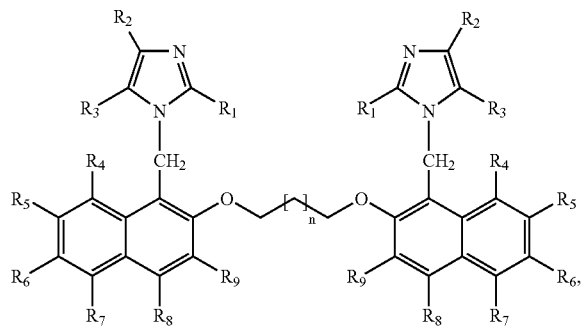

(II)

where
R₁, R₂ and R₃ each independently of one another are H; $C_{1-17}$alkyl;
$C_{3-12}$cycloalkyl, optionally substituted by $C_{1-4}$alkyl groups;
$C_{4-20}$cycloalkyl-alkyl, optionally substituted by $C_{1-4}$alkyl groups;
$C_{6-10}$aryl, optionally substituted by 1-3 $C_{1-4}$alkyl groups, —CN, Hal, OH, or $C_{1-10}$alkoxy;
$C_{7-15}$phenylalkyl, optionally substituted by 1-3 $C_{1-4}$alkyl groups;
$C_{3-12}$alkenyl; $C_{3-12}$alkynyl; or
aromatic or aliphatic $C_{3-17}$acyl;
R₄, R₅, R₆, R₇, R₈ and R₉ each independently of one another are H; $C_{1-17}$alkyl; $C_{3-12}$cycloalkyl, optionally substituted by $C_{1-4}$alkyl groups;
$C_{4-20}$cycloalkyl-alkyl, optionally substituted by $C_{1-4}$alkyl groups;
$C_{6-10}$aryl, optionally substituted by 1-3 $C_{1-4}$alkyl groups;
$C_{7-15}$phenylalkyl, optionally substituted by 1-3 $C_{1-4}$alkyl groups;
$C_{3-17}$alkenyl; $C_{3-12}$alkynyl; $C_{1-12}$alkoxy; or OH; for formula (I)
R is $C_{1-12}$alkyl; $C_{3-12}$cycloalkyl, optionally substituted by $C_{1-4}$alkyl groups;
$C_{4-20}$cycloalkyl-alkyl, optionally substituted by $C_{1-4}$alkyl groups;
$C_{6-10}$aryl, optionally substituted by 1-3 $C_{1-4}$alkyl groups;
$C_{7-15}$phenylalkyl, optionally substituted by 1-3 $C_{1-4}$alkyl groups;
$C_{3-12}$alkenyl; or $C_{3-12}$alkynyl; and for formula (II) n=2-12.

Preferred compounds of the general formulae (I) and (II) in respect of the radicals R₁, R₂ and R₃ are those where R₁, R₂ and R₃ are each independently of one another H;
$C_{1-12}$alkyl; phenyl; or $C_{7-15}$phenylalkyl, optionally substituted by 1-3 $C_{1-4}$alkyl groups; particular preference is given to compounds where R₂ and R₃ are each H; and R₁ is $C_{1-12}$alkyl; phenyl; or $C_{7-15}$phenylalkyl, optionally substituted by 1-3 $C_{1-4}$alkyl groups.

Preferred compounds of the general formula (I) in respect of the radical R are those where R is $C_{1-12}$alkyl; or $C_{3-12}$alkenyl; and preferred compounds of the general formula (II) are those where the factor n=6-12 in respect of the unsubstituted aliphatic —CH₂—(CH₂)ₙ—CH₂— bridge.

Preferred compounds of the general formulae (I) and (II) in respect of the radicals R₄ to R₉ are those for which the stated radicals are a hydrogen atom (H).

The stated preferences for compounds of the general formulae (I) and (II) in respect of the radicals R₁, R₂ and R₃; of the radicals R₄ to R₉; of the radical R for compounds of the general formula (I), and in respect of the factor n for compounds of the general formula (II) also apply in any desired combination.

Particular preference is given to compounds of the general formulae (I) and (II) in which the radicals R₂ to R₉ are a hydrogen atom, and the radical R₁ is $C_{1-4}$alkyl (methyl, ethyl, n,i-propyl, n,i,t-butyl), or phenyl, optionally substituted by 1-3 $C_{1-4}$alkyl groups, and R is $C_{3-12}$alkyl or $C_{3-12}$alkenyl, and for formula (II) n=8, 10, or 12.

Special preference is given to compounds where R₁=methyl, R₂₋₉ are each a hydrogen atom, R=n-butyl, n-nonyl, n-dodecyl, or allyl, and n=8.

The compounds of the invention can be prepared by methods which are known per se. For this purpose, first of all a 1-imidazolylmethyl-substituted 2-naphthol is prepared as described, for example, in EP 0 761 709 A. The hydroxyl group of the naphthol is subsequently etherified by conventional means, preferably in an alkali medium. In the case of the compounds of the formula (II) ring systems which are identical in each case are bridged by an aliphatic, unsubstituted hydrocarbon chain.

As mentioned at the outset, the compounds of the invention are suitable as accelerators for curable epoxy resin systems.

The invention therefore further provides curable epoxy resin compositions comprising
a) an epoxy resin whose epoxide content is from 0.1 to 11, preferably from 0.1 to 2.2, Epoxide equivalents/kg,
b) a compound of the formula (I) or (II),
c) a curing agent for the epoxy resin, and optionally
d) an additive customary in epoxy resin technology.

In principle all epoxy resins are suitable as component (a).

Suitable examples include diglycidyl or polyglycidyl ethers of cycloaliphatic polyols, such as 2,2-bis(4'-hydroxy-cyclohexyl)propane, diglycidyl or polyglycidyl ethers of polyhydric phenols, such as resorcinol, bis(4'-hydroxyphenyl)methane (bisphenol F), 2,2-bis(4'-hydroxyphenyl)-propane (bisphenol A), 2,2-bis(4'-hydroxy-3',5-dibromophenyl) propane, 1,1,2,2-tetrakis(4'-hydroxyphenyl)ethane, or condensation products of phenols with formaldehyde, such as phenol novolaks and cresol novolaks; additionally, di- or poly(β-methylglycidyl) ethers of the above-cited polyalcohols and polyphenols; polyglycidyl esters and poly(β-methylglycidyl)esters of polybasic carboxylic acids such as phthalic acid, terephthalic acid, tetrahydrophthalic and hexahydrophthalic acid; glycidyl derivatives of aminophenols, such as triglycidyl-p-aminophenol; N-glycidyl derivatives of amines, amides and heterocyclic nitrogen bases, such as N,N-diglycidylaniline, N,N-diglycidyltoluidine, N,N,N', N'-tetraglycidyl-bis(4-aminophenyl)methane, triglycidyl isocyanurate, N,N-diglycidyl-N,N'-ethyleneurea, N,N'-diglycidyl-5,5-dimethylhydantoin, N,N'-diglycidyl-5-isopropylhydantoin, N,N'-diglycidyl-5,5-dimethyl-6-isopropyl-5,6-dihydrouracil; polyfunctional epoxy resins, such as the 2,6-disubstituted 4-epoxypropylphenyl glycidyl ethers and adducts thereof that are described in EP-A 205 409 and EP-A 204659; bisphenols such substituted with in each case two glycidyloxy groups and 2,3-epoxypropyl groups, such as the 2,2-bis(3'-epoxypropyl-4'-epoxypropylphenyl)propane described in GB 828364; glycidyl derivatives of tetramethylol-substituted cyclohexanols, cyclohexanones, cyclopentanols and cyclopentanones, such as the compounds described in U.S. Pat. No. 4,549,008; glycidyloxy-substituted benzophenones; and glycidyloxydiketones, such as the compounds described in U.S. Pat. No. 4,649,181.

In general it is also possible to use mixtures of two or more epoxy resins as components in the formulations of the invention.

Suitable epoxy resins include preferably glycidyl ethers such as bisphenol A or F, glycidyl esters, N-glycidyl and N,O-glycidyl derivatives of aromatic or heterocyclic compounds, and also cycloaliphatic glycidyl compounds. They preferably have a functionality of from 0.1 to 2.2 epoxide equivalents/kg.

As curing agents, or component (c), it is possible in principle to use all of the curing agents which are customary in epoxy resin chemistry, such as amines, dicyandiamide, cyanoguanidines, melamines, novolaks, including cresol-novolaks, polyols and anhydrides, for example.

Curing agents suitable in principle also include the dihydroxy aromatics such as the bisphenols or diphenols already mentioned. Besides diphenols R is also possible to use triphenols or polyphenols, such as 2,4,6-tris[2'-(p-hydroxyphenyl)-2'-propyl]benzene (from Mitsui Petrochemical), for example.

As curing agent it is preferred to use amines and polyamines, examples being those of the Jeffamine D and T type, and others. Examples that may be mentioned include o-, m-, and p-phenylenediamine; diaminotoluenes, such as 2,4-diaminotoluene, 1,4-diamino-2-methoxy-benzene, 2,5-diaminoxylene, 1,3-diamino-4-chlorobenzene, 4,4'-diaminodiphenylmethane, 4,4'-diaminodiphenyl ether, 4,4'-diaminodiphenyl thioether, 4,4'-diaminodiphenyl sulfone, 2,2'-diaminobenzophenone, 1,8- or 1,5-diaminonaphthalene, 2,6-diaminopyridine, 1,4-piperazine, 2,4-diaminopyrimidine, 2,4-diamino-s-triazine, di-, tri-, tetra, hexa-, hepta-, octa-, and decamethylenediamine, 3-methylheptamethylene-1,6-diamine, 3-methoxyhexamethylenediamine, 2,11-diaminododecane, 2,2,4- and 2,4,4-trimethylhexamethylenediamine, 1,2-bis(3-aminopropoxy)ethane, N,N'-dimethylethylenediamine, N,N'-dimethyl-1,6-diaminohexane and also the diamines of the formulae $H_2N(CH_2)_3O(CH_2)_2O(CH_2)_3—NH_2$ and $H_2N(CH_2)_3S(CH_2)_3NH_2$, 1,4-diaminocyclohexane, 1,4-bis(2-methyl-4-aminopentyl)benzene, 1,4-bis(aminomethyl)benzene.

Additionally suitable amines are carbocyclic-aromatic diamines, especially substituted dinuclear diamines, such as bis(3,5-diisopropyl-4-aminophenyl)methane, bis(2-chloro-3,5-di-ethyl-4-aminophenyl)methane, bis(3-ethyl-4-amino-5-sec-butylphenyl)methane, bis(2-chloro-3,5-diethyl-4-aminophenyl)methane and bis(3,5-diethyl-4-aminophenyl)methane, for example.

Additionally suitable are propane-1,3-diamine, m-xylenediamine, bis(4-aminocyclohexyl)-propane, 3-aminomethyl-3,5,5-trimethylcyclohexylamine(isophoronediamine), polyaminoamides, examples being those consisting of aliphatic polyamines and dimerized or trimerized fatty acids; polyphenols, such as resorcinol, hydroquinone, bisphenol A and phenol/aldehyde resins, and also polythiols such as "Thiokols" for example.

Preferred curing agents are diamines or polyamines, amino-terminated polyalkylene glycols (e.g. Jeffamines, amino-poly-THF) or polyaminoamides, especially dimers or copolymers of propylene glycol and ethylene glycol, amino-terminated polybutadienes with molecular weights in the range from about 150 to 5000, in particular from 200 to 600.

Particularly preferred curing agents am amino-terminated polyetherdiamines, especially short-chain polyoxyalkylenediamines with a small (less than 10, preferably less than 6) repetition factor in respect of the polyoxyalkylene units. As commercially available curing agents mention may be made of Jeffamine® D230, a polyoxypropylenediamine containing on average 2.6 oxypropylene units.

As optional component d) it is possible to use additives customary in epoxy resin technology. By these are meant the customary auxiliaries and additives which are known to and used by the person skilled in the art in respect of the particular application. Examples include organic and inorganic fillers and pigments, release agents, and viscosity-influencing additives.

To prepare the curable compositions of the invention the accelerators of the invention are dissolved beforehand in the curing agent, at generally elevated temperatures: for example, when using a Jeffamine®, at about 80° C. Solutions of this kind can be cooled to 40° C. and then mixed with the epoxy resin. These mixtures can then be used directly as an RTM or impregnating solution. Another possibility is to disperse the accelerators of the invention homogeneously in the epoxy resin beforehand, by means for example of suitable stirrers, such as an Ultra-Turrax or a triple roll mill.

The compounds of the invention are used advantageously at from 1 to 10 parts by weight, based on the overall formulation. It is particularly advantageous to use from 5 to 7 parts by weight. The curing agents are employed in the customary amounts, which are therefore to be calculated such that on average per epoxide group there are from 0.5 to 1.5, preferably from 0.8 to 1.2, functional groups of the curing agent. Auxiliaries and additives can be used in principle in wide quantity ranges, provided that this is possible without a significant increase in the viscosity of the desired compositions.

As already mentioned, the compounds of the invention lower the storage stabilities of prepregs when they are used, for example, in epoxy resin/amine formulations and the prepregs thus prepared are stored at room temperature. However, prepregs comprising inventive accelerators of this kind have the capacity to give an ILS value of up 50 MPa. Accordingly the accelerators of the invention are particularly suitable for use in epoxy resin formulations which are employed as compression moulding compounds, sinter powders, encapsulating systems, casting resins and for producing prepregs and laminates by the resin infusion method, wet layup method and injection methods.

EXPERIMENTAL SECTION a) Preparation of the Mannich Bases. General Description of the Etherification of a Naphthol, Using 1-imidazotlymethyl-2-naphthol as Example. Alkaline Variant in DMSO.

A sulphonating flask (300-400 ml) provided with reflux condenser, internal thermometer, dropping funnel and KPG stirrer is charged with dimethyl sulphoxide and then the chosen naphthol is added with stirring. This gives a beige suspension. KOH in powdered form is added to the stirred solution. The solution changes its colour from beige to green and clarifies over the course of about 15 minutes to form a deep-green solution which still contains a few solid fractions. The internal temperature within the flask is approximately 22° C. At this temperature the alkyl halogen or the alkyl dihalogen, respectively, is added dropwise. The mixture is warmed to 30° C. over 15 minutes. Then the remaining haloalkyl or dihaloalkyl is added over a further nine minutes. The contents of the flask are heated initially to just over 50° C. and then to about 70° C. The flask is stirred at this temperature for two-three hours. Thereafter the reaction solution is poured onto 150 g of ice. A beige-brown solid and a milky aqueous phase are obtained. The organic phase is separated from the aqueous phase and the latter is extracted by shaking five times with 50 ml of toluene each time. The combined organic phases are dried over anhydrous sodium sulphate. After overnight standing and the removal of the drying agent on a suction filter, the solvent is removed on a rotary evaporator. This crude product is taken up in 20 ml of isopropanol and heated under reflux to about 65° C. The product is frozen out of the solution using dry ice, and isopropanol is removed on a suction filter. Finally the solid is dried at about 40° C./0.3 mbar for about two hours. The amounts of the individual components used can be found in Table 1 below.

TABLE 1

| E[1] | Comp. 1[2] | Comp. 2[2] | Comp. 3[2] | Solv.[3] | Yld.[4] | M.p[5] |
|---|---|---|---|---|---|---|
| 1 | 11.91 (50) | 10.56 (51) | 3.08 (55) | 100 | 80-86 | 83 |
| 2 | 35.73 (150) | 18.91 (153) | 9.24 (165) | 300 | 37 | 93 |
| 3 | 35.73 (150) | 38.13 (153) | 9.24 (165) | 300 | 91 | 81 |
| 4 | 35.73 (150) | 14.16 (153) | 9.24 (165) | 300 | 85 | 91 |
| 5 | 28.59 (120) | 18.0 (60) | 7.08 (126) | 300 | 48 | 158 |

[1]E = experiment;
[2]Comp. = component, amount in g and mmol ( ), component 1 = 1-imidazolylmethyl-2-naphthol, component 2 for E1 = nonyl bromide, E2 = allyl bromide, E3 = dodecyl bromide, E4 = butyl chloride, E5 = 1,10-dibromododecane; component 3 = KOH
[3]Solv. = solvent in ml, solvent in above experiments is in each case dimethyl sulphoxide (DMSO);
[4]Yld. = yield in %;
[5]m.p = melting point (DSC) in ° C. Further characterization of the products was by $^1$H and $^{13}$C NMR ($d_6$-DMSO) and C, H, N, O analyses.

The compounds of the invention are advantageously added in from 1 to 10 parts, in particular from 5 to 7 parts, by weight to the desired formulation. See also Table 2 in this regard.

b) Use Examples of the Mannich Bases of the Invention

The products from the above experimental section a) are dissolved at temperatures between 60° C. and 80° C. in the amine curing agent. This gives orange to dark brown clear solutions. After cooling to room temperature, this solution is admixed with the calculated amount of epoxy resin. For details see Table 2 below:

TABLE 2

| Experiment | Comparison | E6 | E7 | E8 | E9 | E10 |
|---|---|---|---|---|---|---|
| LY 556[1] | 100 | 100 | 100 | 100 | 100 | 100 |
| Jeffamine[2] | 10 | 10 | 10 | 10 | 10 | 8 |
| Accelerator[3] | 10 | | | | | |
| E1[4] | | 7 | | | | |
| E2[4] | | | 5 | | | |
| E3[4] | | | | 5 | 5 | 3 |
| DY 965[5] | | | | 5 | 10 | |
| Minimum viscosity at 60° C. [mPa·s][12] | 800-1000 | 150 | 150 | 150 | Ng[11] | 150 |
| Preparation[6] | 8 | 2-7 | 2 | 2 | 2 | 2 |
| Prepreg[7] | 12 | 12 | ? | 12 | 12 | 12 |
| Resin content[8] | 40-42 | 40-42 | 40-42 | 40-42 | 40-42 | 40-42 |
| Storage[9] | RT | RT | RT | RT | RT | RT |
| Interlaminar shear strength (ILS) after 30 min at 140° C.: | | | | | | |
| $F_{max}$ [N][10] | 601 +/– 38 | 2067 +/– 52 | 2109 +/– 52 | 1201 +/– 33 | 989 +/– 62 | 1037 +/– 20 |
| $\sigma_{max}$ [MPa][10] | 22.6 +/– 1.4 | 50.9 +/– 1.2 | 52 +/– 0.7 | 44.2 +/– 1.5 | 38.2 +/– 2.5 | 34.6 +/– 0.7 |
| Interlaminar shear strength (ILS) after 4 h at 75° C.: | | | | | | |
| $F_{max}$ [N] | 426 +/– 37 | 496 +/– 30 | Ng | 964 +/– 73 | 1074 +/– 35 | 1082 +/– 29 |
| $\sigma_{max}$ [MPa] | 16.0 +/– 1.4 | 13.4 +/– 0.7 | Ng | 38.1 +/– 1.8 | 40.3 +/– 0.9 | 40.6 +/– 1.3 |
| Interlaminar shear strength (ILS) after 8 h at 75° C.: | | | | | | |
| $F_{max}$ [N] | 400 +/– 33 | 1271 +/– 125 | Ng | 959 +/– 48 | 927 +/– 36 | 1182 +/– 102 |
| $\sigma_{max}$ [MPa] | 16.0 +/– 1.3 | 43.0 +/– 4.0 | Ng | 38.6 +/– 1.7 | 37.7 +/– 1.3 | 45.4 +/– 3.3 |
| Interlaminar shear strength (ILS) after 4 h at 60° C.: | | | | | | |
| $F_{max}$ [N] | Nm[11] | 2132 +/– 14 | Ng | Ng | Ng | Ng |
| $\sigma_{max}$ [MPa] | Nm[11] | 50 +/– 0.4 | Ng | Ng | Ng | Ng |

[1]Araldite LY 556 Bisphenol-A Harz (Vantico AG)
[2]Jeffamine Jeffamine D-230 (Huntsman)
[3]XU 3123 1-Imidazolylmethyl-2-naphthol (Vantico AG)
[4]E1/E2/E3 Experiments 1, 2 and 3 (see Table 1)
[5]DY 965 Flexibilizing agent DY 965 (Vantico AG)
[6]Preparation Preparation of the prepregs and laminates after number of days
[7]Prepreg Number of plies = 12
[8]Resin content1 Resin content in per cent after compression of the laminates
[9]Storage At 20° C. to 25° C. = RT
[10]$F_{max}$ Ultimate strength (breaking load) to ASTM D 2344
$\sigma_{max}$ Shear strength to ASTM D 2344
[11]Nm, Ng Nm = not measurable, Ng = not measured
[12]Viscosity Determined using Rheometrix RD2 with a plate/plate setup Surprising are the very good interlaminar shear strengths which can be obtained with the accelerators of the invention in the lower temperature range (60° C. and 75° C./48 hours), see Table 2, Formulations E6, E7 and Comparison. The values found are substantially higher than in the case of the comparison system. The viscosity level of 150 mPa·s which can be achieved with the accelerators of the invention at 60° C. is also well below that of the comparison system, of 800-1000 mPa·s at 60° C. This is a key further advantage of the accelerators of the invention with a view to their use in infusion methods, since low viscosities are required therein.

The invention claimed is:

1. A compound of general formula (I) or (II):

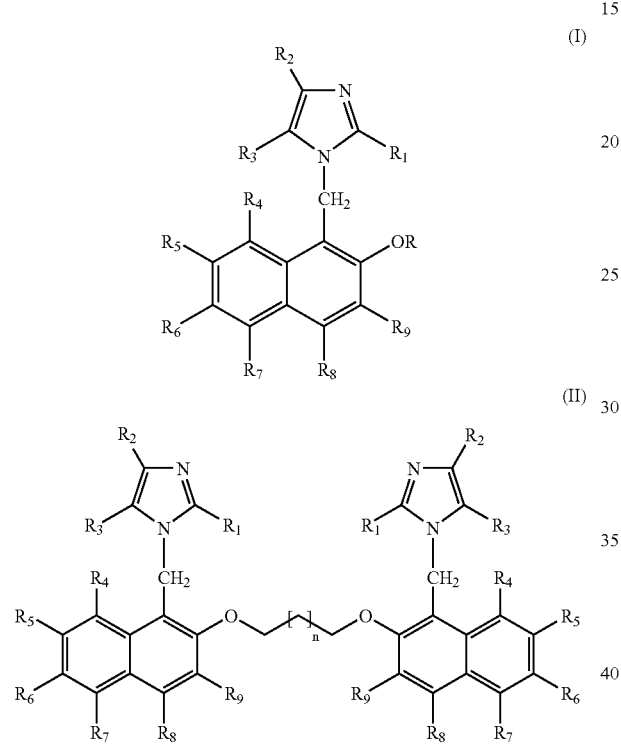

where
  $R_1$, $R_2$, and $R_3$ each independently of one another are H; $C_{1-7}$ alkyl; $C_{3-12}$ cycloalkyl, optionally substituted by $C_{1-4}$ alkyl groups; $C_{4-20}$ cycloalkyl-alkyl, optionally substituted by $C_{1-4}$ alkyl groups; $C_{6-10}$ aryl, optionally substituted by 1-3 $C_{1-4}$ alkyl groups, —CN, Hal, OH, or $C_{1-10}$ alkoxy; $C_{7-15}$ phenylalkyl, optionally substituted by 1-3 $C_{1-4}$ alkyl groups; $C_{3-12}$ alkenyl; $C_{3-12}$ alkynyl; or aromatic or aliphatic $C_{3-12}$ acyl;
  $R_4$, $R_5$, $R_6$, $R_7$, $R_8$ and $R_9$ each independently of one another are H; $C_{1-17}$ alkyl; $C_{3-12}$ cycloalkyl, optionally substituted by $C_{1-4}$ alkyl groups; $C_{4-20}$ cycloalkyl-alkyl, optionally substituted by $C_{1-4}$ alkyl groups; $C_{6-10}$ aryl, optionally substituted by 1-3 $C_{1-4}$ alkyl groups; $C_{7-15}$ phenylalkyl, optionally substituted by 1-3 $C_{1-4}$ alkyl groups; $C_{3-17}$ alkenyl; $C_{3-12}$ alkynyl; $C_{1-12}$ alkoxy or OH;
  for formula (I) R is $C_{1-12}$ alkyl or $C_{3-12}$ alkenyl;
  and for formula (II) n=2-12.

2. A compound according to claim 1, where $R_1$, $R_2$ and $R_3$ each independently of one another are H; $C_{1-17}$ alkyl; phenyl; or $C_{7-15}$ phenylalkyl, optionally substituted by 1-3 $C_{1-4}$ alkyl groups.

3. A compound according to claim 2, where $R_2$ and $R_3$ each H; and
  $R_1$ is $C_{1-17}$ alkyl; phenyl; or $C_{7-15}$ phenylalkyl, optionally substituted by 1-3 $C_{1-4}$ alkyl groups.

4. A compound according to claim 1, where Formula (II) n=6-12.

5. A compound according to claim 1, where $R_4$, $R_5$, $R_6$, $R_7$, $R_8$ and $R_9$ are H.

6. A compound according to claim 1, where $R_1$ is methyl; $R_2$, $R_3$, $R_4$, $R_5$, $R_6$, $R_7$, $R_8$ and $R_9$ are H;
  R is n-butyl, n-nonyl, n-dodecyl, or allyl; and
  n=8.

7. A curable composition comprising:
  a) an epoxy resin whose epoxide content is from 0.1 to 11 epoxide equivalents/kg;
  b) from 1 to 10 parts by weight, based on the total weight of the curable composition, of a compound of formula (I) or (II):

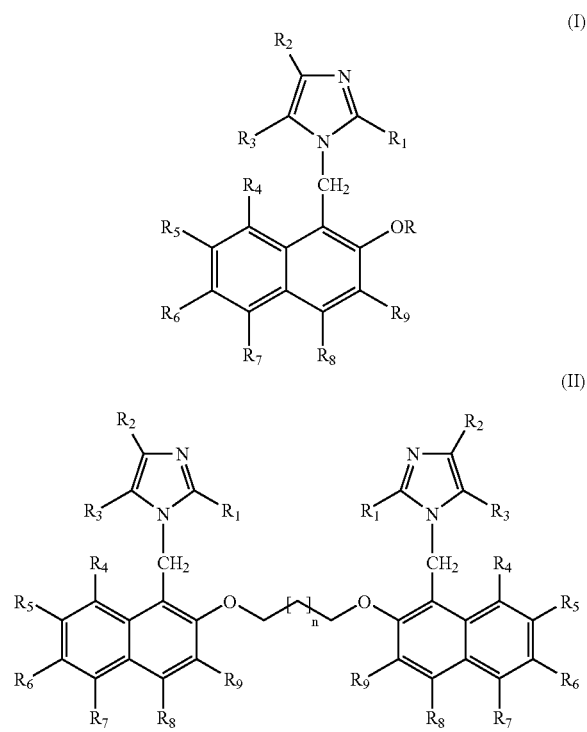

where
  $R_1$, $R_2$, and $R_3$ each independently of one another are H; $C_{1-17}$ alkyl; $C_{3-12}$ cycloalkyl, optionally substituted by $C_{1-4}$ alkyl groups; $C_{4-20}$ cycloalkyl-alkyl, optionally substituted by $C_{1-4}$ alkyl groups; $C_{6-10}$ aryl, optionally substituted by 1-3 $C_{1-4}$ alkyl groups, —CN, Hal, OH, or $C_{1-10}$ alkoxy; $C_{7-15}$ phenylalkyl, optionally substituted by 1-3 $C_{1-4}$ alkyl groups; $C_{3-12}$ alkenyl; $C_{3-12}$ alkynyl; or aromatic or aliphatic $C_{3-12}$ acyl; $R_4$, $R_5$, $R_6$, $R_7$, $R_8$ and $R_9$ each independently of one another are H; $C_{1-17}$ alkyl; $C_{3-12}$ cycloalkyl, optionally substituted by $C_{1-4}$ alkyl groups; $C_{4-20}$ cycloalkyl-alkyl, optionally substituted by $C_{1-4}$ alkyl groups; $C_{6-10}$ aryl, optionally substituted by 1-3 $C_{1-4}$ alkyl groups; $C_{7-15}$ phenylalkyl, optionally substituted by 1-3 $C_{1-4}$ alkyl groups; $C_{3-17}$ alkenyl; $C_{3-12}$ alkynyl; $C_{1-2}$ alkoxy or OH;

for formula (I) R is $C_{1-12}$ alkyl; $C_{3-12}$ cycloalkyl, optionally substituted by $C_{1-4}$ alkyl groups; $C_{4-20}$ cycloalkyl-alkyl, optionally substituted by $C_{1-4}$ alkyl groups; $C_{6-10}$ aryl, optionally substituted by 1-3 $C_{1-4}$ alkyl groups; $C_{7-15}$ phenylalkyl, optionally substituted by 1-3 $C_{1-4}$ alkyl groups; $C_{3-12}$ alkenyl or $C_{3-12}$ alkynyl; and for formula (II) n=2-12;

c) a curing agent for the epoxy resin having from 0.5 to 1.5 functional groups per epoxide group; and optionally d) one or more additives.

8. A curable composition according to claim 7, wherein the curing agent is an amine or polyamine.

9. A curable composition according to claim 8, wherein the curing agent is a polyoxypropylenediamine.

10. A curable composition according to claim 7, wherein the epoxy resin is a glycidyl ether, glycidyl ester, N-glycidyl or N,O-glycidyl derivative of an aromatic or heterocyclic compound, or a cycloaliphatic glycidyl compound.

11. A prepreg comprising a curable composition according to claim 7.

12. A method for making a curable composition comprising adding to an epoxy resin a curing agent and a compound of formula (I) or (II):

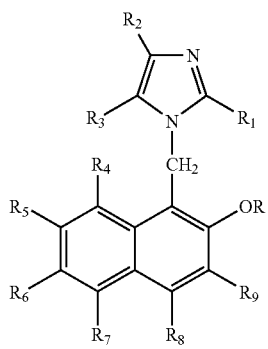

(I)

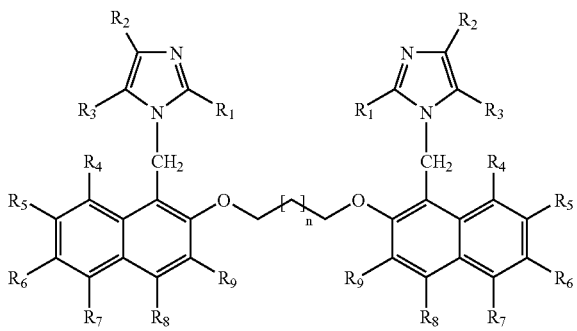

(II)

where $R_1$, $R_2$, and $R_3$ each independently of one another are H; $C_{1-17}$ alkyl; $C_{3-12}$ cycloalkyl, optionally substituted by $C_{1-4}$ alkyl groups; $C_{4-20}$ cycloalkyl-alkyl, optionally substituted by $C_{1-4}$ alkyl groups; $C_{6-10}$ aryl, optionally substituted by 1-3 $C_{1-4}$ alkyl groups, —CN, Hal, OH, or $C_{1-10}$ alkoxy; $C_{7-15}$ phenylalkyl, optionally substituted by 1-3 $C_{1-4}$ alkyl groups; $C_{3-12}$ alkynyl; $C_3$ alkynyl; or aromatic or aliphatic $C_{3-12}$ acyl;

$R_4$, $R_5$, $R_6$, $R_7$, $R_8$ and $R_9$ each independently of one another are H; $C_{1-17}$ alkyl; $C_{3-12}$ cycloalkyl, optionally substituted by $C_{1-4}$ alkyl groups; $C_{4-20}$ cycloalkyl-alkyl, optionally substituted by $C_{1-4}$ alkyl groups; $C_{6-10}$ aryl, optionally substituted by 1-3 $C_{1-4}$ alkyl groups; $C_{7-15}$ phenylalkyl, optionally substituted by 1-3 $C_{1-4}$ alkyl groups; $C_{3-17}$ alkenyl; $C_{3-12}$ alkynyl; $C_{1-12}$ alkoxy or OH;

for formula (I) R is $C_{1-12}$ alkyl; $C_{3-12}$ cycloalkyl, optionally substituted by $C_{1-4}$ alkyl groups; $C_{4-20}$ cycloalkyl-alkyl, optionally substituted by $C_{1-4}$ alkyl groups; $C_{6-10}$ aryl, optionally substituted by 1-3 $C_{1-4}$ alkyl groups; $C_{7-15}$ phenylalkyl, optionally substituted by 1-3 $C_{1-4}$ alkyl groups; $C_{3-12}$ alkenyl or $C_{3-12}$ alkynyl; and for formula (II) n=2-12.

13. The method of claim 12 wherein the compound of formula (I) or (II) is dissolved beforehand in the curing agent at a temperature between 60°-80° C.

\* \* \* \* \*